(12) United States Patent
Keng

(10) Patent No.: US 7,060,044 B2
(45) Date of Patent: Jun. 13, 2006

(54) MASSAGE DEVICE FOR ATTACHING ONTO USERS

(76) Inventor: Chi Fang Keng, P.O. Box 10-69, Chong Ho, Taipei (TW)

( * ) Notice: Subject to any disclaimer, the term of this patent is extended or adjusted under 35 U.S.C. 154(b) by 0 days.

(21) Appl. No.: 10/188,635

(22) Filed: Jun. 29, 2002

(65) Prior Publication Data

US 2004/0002669 A1  Jan. 1, 2004

(51) Int. Cl.
*A61H 15/00* (2006.01)

(52) U.S. Cl. .......................... 601/151; 601/15; 601/148

(58) Field of Classification Search .................. 601/15, 601/16, 17, 148, 149, 150, 151, 152, 160, 601/165, 166, 168; 5/654, 655.3, 713, 714; 128/DIG. 20

See application file for complete search history.

(56) References Cited

U.S. PATENT DOCUMENTS

| | | | | |
|---|---|---|---|---|
| 3,778,851 A * | 12/1973 | Howorth | ...................... | 601/148 |
| 4,175,297 A * | 11/1979 | Robbins et al. | ............. | 601/148 |
| 5,056,505 A * | 10/1991 | Warwick et al. | ............... | 601/44 |
| 5,603,690 A * | 2/1997 | Barry | .......................... | 601/148 |
| 5,938,627 A * | 8/1999 | Hickman | .................... | 601/149 |
| 6,254,556 B1 * | 7/2001 | Hansen et al. | .............. | 601/149 |
| 6,393,633 B1 * | 5/2002 | Ferber | ......................... | 601/154 |

* cited by examiner

*Primary Examiner*—Quang D. Thanh

(57) ABSTRACT

A massage device includes a mat device having a chamber formed between two layers for receiving fluid and for supporting users, and having a groove formed in the middle portion for engaging onto the users' heads and for attaching the mat device onto the users. A container is used for receiving the fluid and coupled to the inlet and the outlet of the mat device, and a pump is used for pumping the fluid into and out of the chamber of the mat device. The mat device has one or more seals formed between the layers for forming a fluid passage in the mat device.

1 Claim, 5 Drawing Sheets

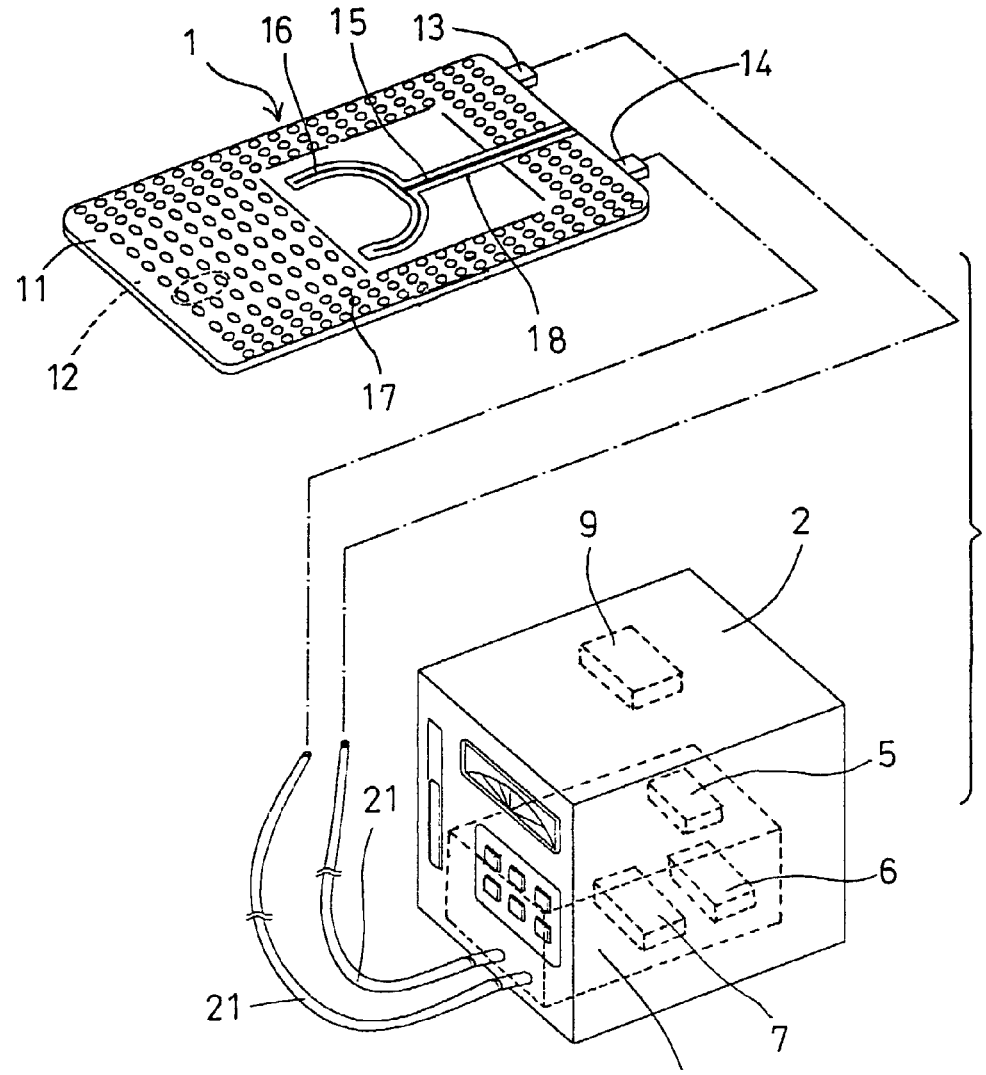
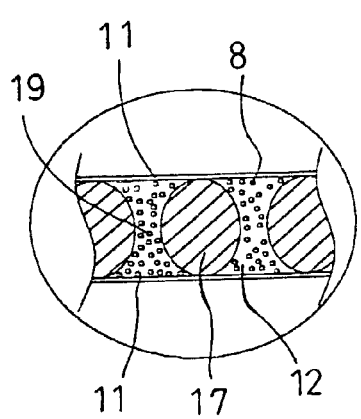
FIG. 2
FIG. 3

MASSAGE DEVICE FOR ATTACHING ONTO USERS

BACKGROUND OF THE INVENTION

1. Field of the Invention

The present invention relates to a massage device, and more particularly to a massage device for supporting the users and for attaching onto the users.

2. Description of the Prior Art

Typical inflatable air mattresses have been developed and provided for supporting patients, and/or for moving or tossing or turning or massaging the patients. However, the air mattresses may not be used for applying or for transmitting heat to warm the users. In addition, the typical air-mattress type massage devices may not be attached onto the users.

The present invention has arisen to mitigate and/or obviate the afore-described disadvantages of the conventional massage devices.

SUMMARY OF THE INVENTION

The primary objective of the present invention is to provide a massage device for supporting and massaging the users and/or for selectively attaching onto the users.

The other objective of the present invention is to provide a massage device for applying or transmitting heat to the users.

In accordance with one aspect of the invention, there is provided a massage device comprising a mat device including a chamber formed between two layers, for receiving fluid therein and for supporting users thereon, and including an inlet and an outlet, the mat device including a middle portion having a groove formed therein, and a seal formed around the groove, for allowing a user's head to engage through the groove of the mat device, and to engage the mat device onto the user, and means for pumping fluid into and out of the chamber of the mat device.

The mat device includes at least one seal formed and provided therein for forming a fluid passage therein, the fluid passage of the mat device includes two ends communicating with the inlet and the outlet of the mat device.

The groove of the mat device is preferably U-shaped and located close to the at least one seal of the mat device for forming a Y-shaped structure.

The mat device includes a plurality of blocks disposed in the chamber thereof for narrowing the chamber of the mat device. The blocks are preferably secured between the layers of the mat device and having gaps formed between the blocks.

The pumping means includes a container for receiving the fluid and coupled to the inlet and the outlet of the mat device, and a pump for pumping the fluid into and out of the chamber of the mat device.

A heat device may further be provided and disposed in the container for heating the fluid. A far infrared device may further be provided and disposed in the container for releasing far infrared material into the fluid. A processor device may further be provided and coupled to the pump for controlling the pump.

Further objectives and advantages of the present invention will become apparent from a careful reading of a detailed description provided hereinbelow, with appropriate reference to accompanying drawings.

BRIEF DESCRIPTION OF THE DRAWINGS

FIG. 2 is a partial exploded view of the massage device;

FIG. 3 is a partial cross sectional view of the mat device;

DETAILED DESCRIPTION OF THE PREFERRED EMBODIMENT

Figure 4:
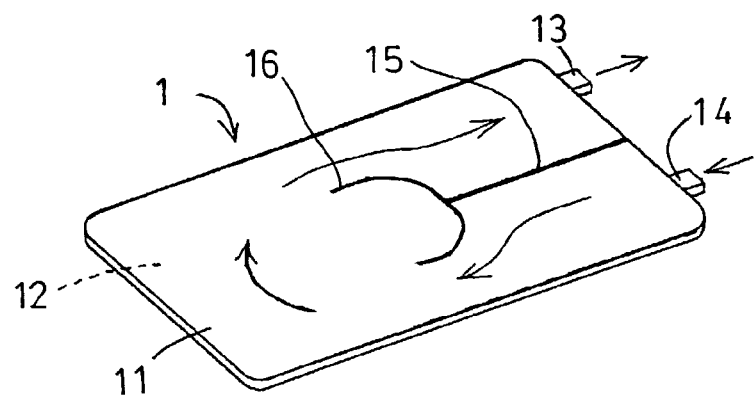
FIG. 4 is a top plan view of the mat device, illustrating the operation of the massage device.
Figure 5:
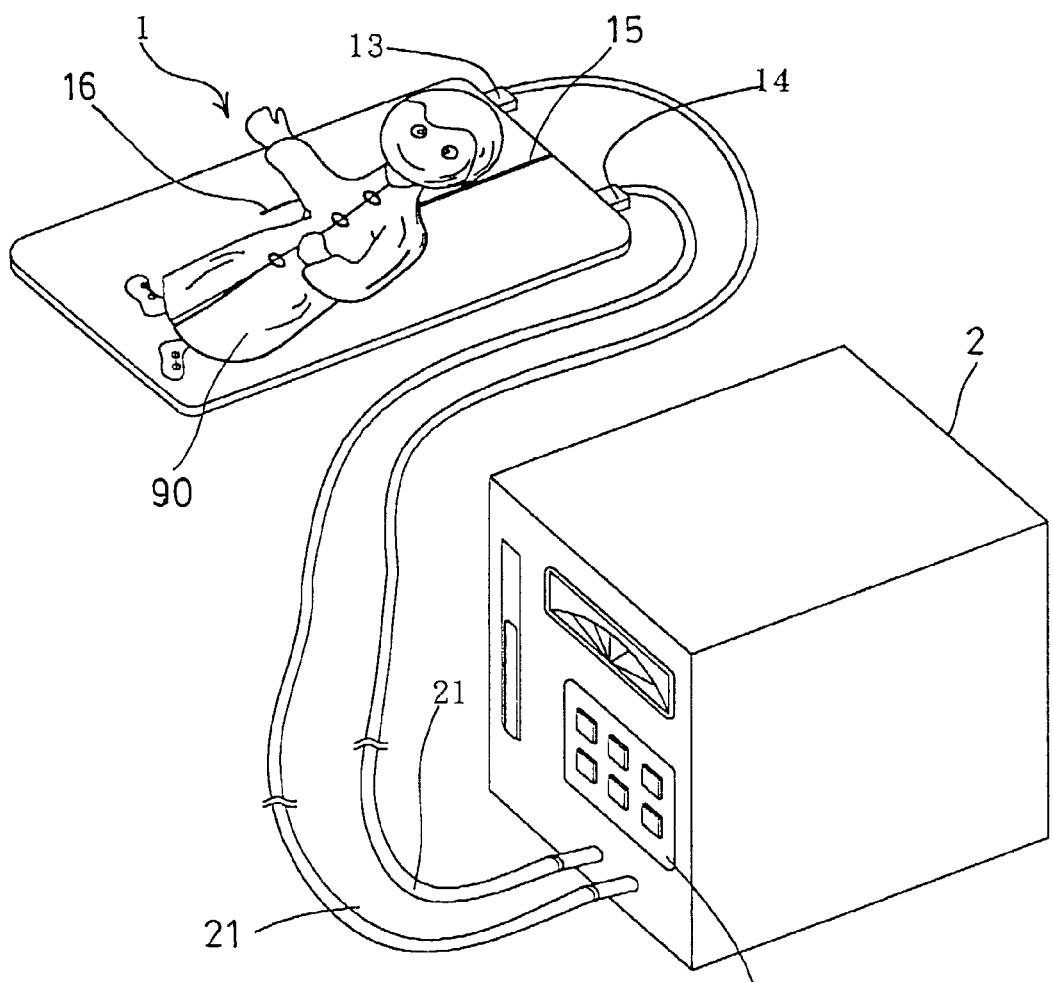
FIGS. 5, 6, 7 are perspective views illustrating the operation of the massage device.
Figure 6:
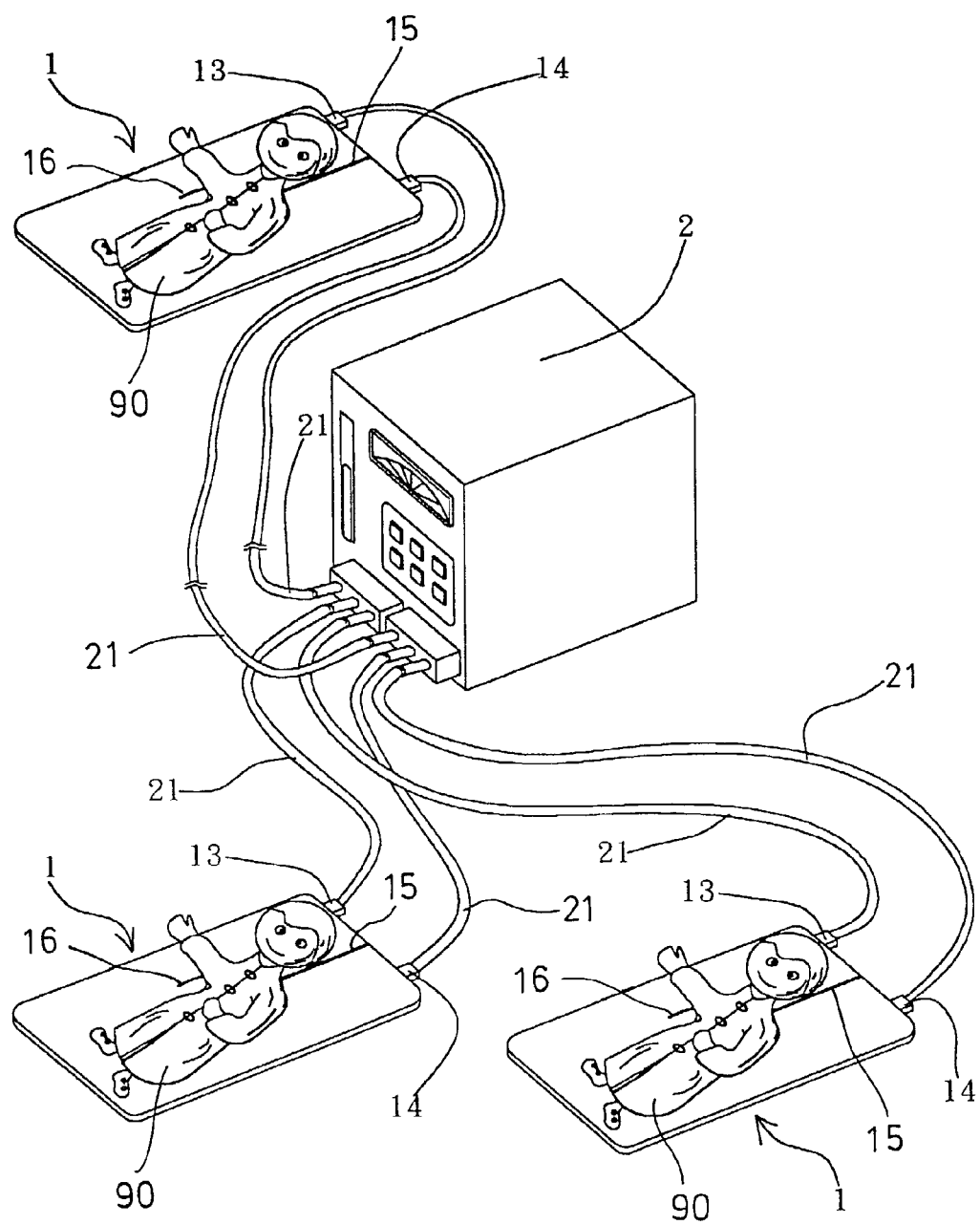

Referring to the drawings, and initially to FIGS. 1–4, a massage device in accordance with the present invention comprises a mat device 1 including a planar structure having a chamber 12 formed between two layers 11, for receiving air or fluid 8 therein (FIG. 3), such as water, and for supporting the users 90 on the mat device 1, best shown in FIGS. 5, 6.

The mat device 1 includes a longitudinal seal 15 formed in one end portion, and secured or sealed between the two layers 11, and having one end extended toward one end of the mat device 1, and the other end extended toward the middle or center portion of the mat device 1, for forming a substantially U-shaped flowing passage in the mat device 1, best shown in FIG. 4.

The mat device 1 includes an inlet 13 and an outlet 14 formed or provided therein and provided or coupled to the two ends of the substantially U-shaped flowing passage in the mat device 1, that is formed or defined by the longitudinal seal 15, for allowing the fluid 8 to flow into and out of the chamber 12 of the mat device 1.

The mat device 1 further includes a substantially U-shaped groove 16 formed in the middle portion thereof and located close to or adjacent to the seal 15 for forming a Y-shaped structure. The mat device 1 includes a peripheral seal 18 formed along the sides of the groove 16 and/or the seal 15, for making a water-tight seal around the groove 16 of the mat device 1.

Figure 7:
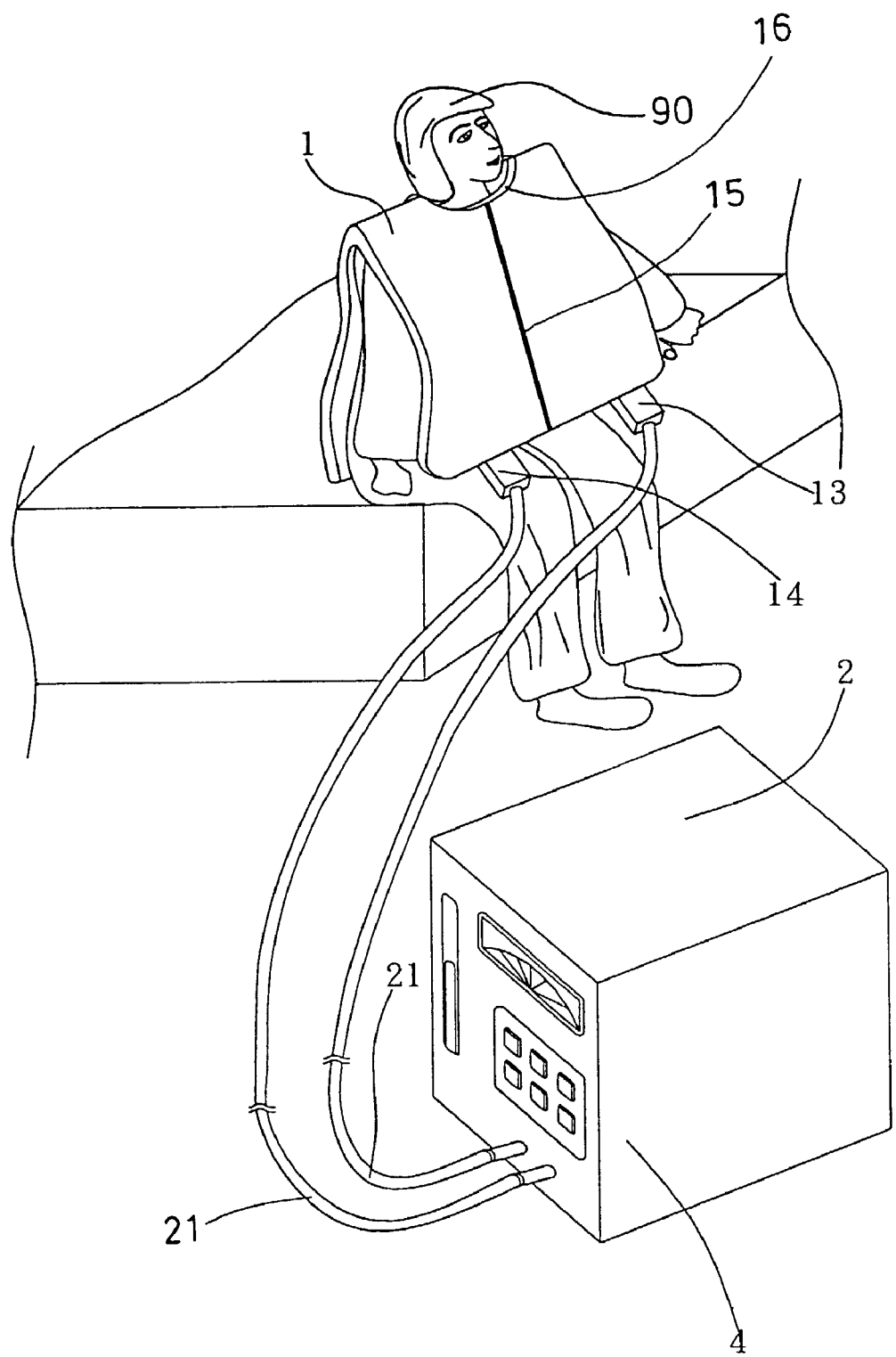

In operation, as shown in FIG. 7, the user may wear the mat device 1 by engaging his head into or through the, groove 16 of the mat device 1, such that the mat device 1 may be attached onto the user as a cape or a shawl.

As shown in FIG. 3, a number of particles or pins or posts or blocks 17 or the like may further be provided and engaged in or arranged in the chamber 12 of the mat device 1, and preferably secured between the two layers 11, and having slots or gaps 19 formed between the blocks 17, for narrowing the fluid passage or the chamber 12 of the mat device 1.

A control device 2 is further provided and includes a container 4 disposed therein for receiving the fluid 8 therein, and coupled to the inlet 13 and the outlet 14 of the mat device 1 with pipes or hoses 21, for allowing the fluid 8 to flow between the container 4 and the chamber 12 of the mat device 1.

As shown in FIG. 2, a heat device 6 may further be provided and disposed in the container 4 for heating the fluid, and then for applying or transmitting the heat to the users. A pump 5 may be disposed in the control device 2 or in the container 4 for pumping the fluid into and out of the mat device 1.

Figure 1:
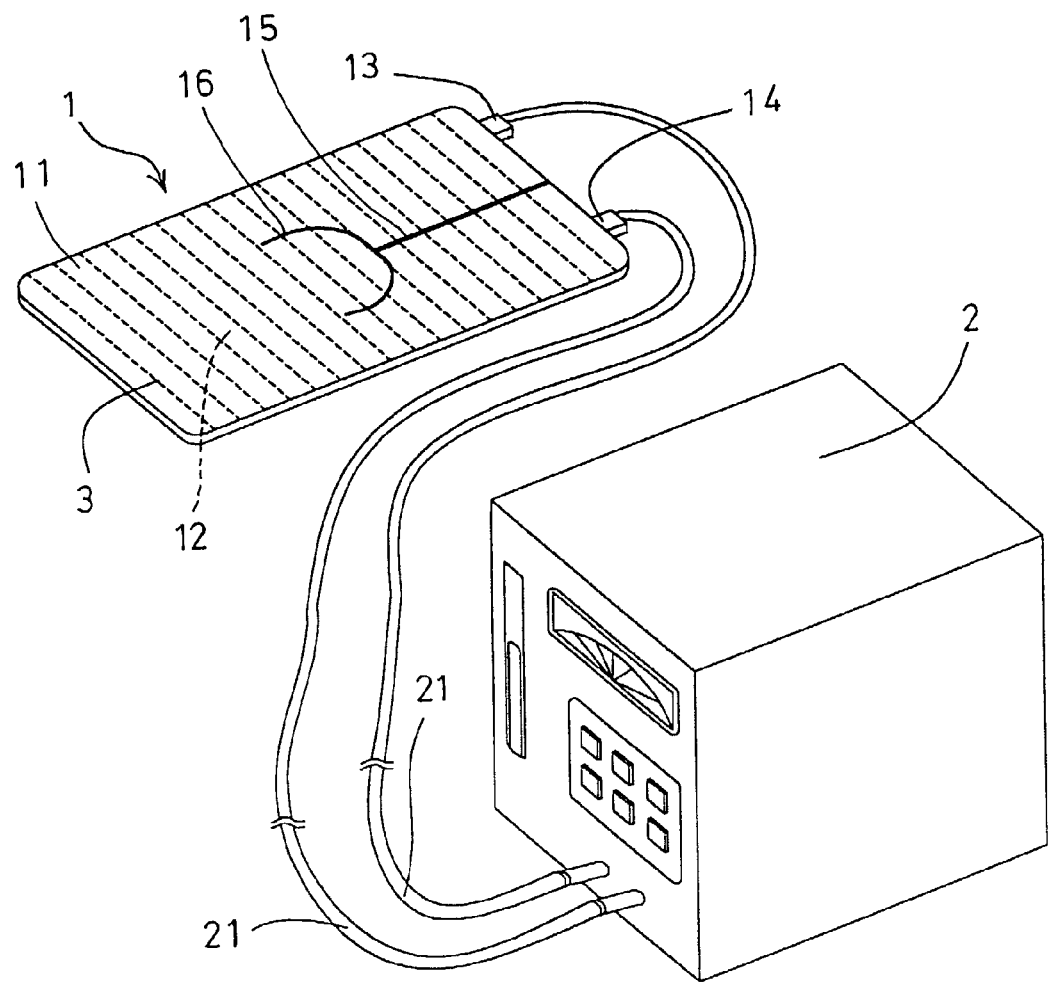
FIG. 1 is a perspective view of a massage device in accordance with the present invention, in which a mat device is disposed up-side-down.

As shown in FIG. 1, the mat device 1 may include a portion, such as the lower portion thereof having a far infrared material 3 engaged or applied or disposed therein for facilitating the blood circulation of the users. A far infrared device 7 may further be disposed in the container 4 for releasing far infrared material into the fluid, for example.

A control or processor device 9 may further be provided for controlling the operation of the pump 5, and/or for controlling the heat device 6 to heat the fluid to the suitable temperature, and/or the far infrared device 7. The processor device 9 may shut off the pump 5 and the heat device 6 when the water quantity in the container 4 is below a predetermined level or value or the like.

The control device 2 may be energized by batteries, such as the batteries of the vehicles, or the other batteries, or may include a coupler or a plug for coupling to the socket of the vehicle, or for coupling to the sockets of the house buildings, so as to be energized by various electric power sources.

In operation, as shown in FIGS. 5, 6, the container 4 of the control device 2 may be coupled to one or more mat devices 1, for pumping the fluid through the chamber 12 or the fluid passages of the mat devices 1, in order to support and/or to massage or move or toss or turn the patients, and/or may apply or transmit the heat to the patients. The pump 5 may thus form a pumping means for pumping the fluid into and out of the mat device 1.

As shown in FIG. 7, the user may wear the mat device 1 by engaging his head into or through the groove 16 of the mat device 1, and the mat device 1 may thus be attached onto the user as a cape or a shawl and may thus be moved along with the users. The fluid pumped through the chamber 12 or the fluid passages of the mat devices 1 may also be used to massage the users.

Accordingly, the massage device in accordance with the present invention may be used for supporting and massaging the users and/or for selectively attaching onto the users, and/or for applying or transmitting heat to the users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A massage device comprising: a mat device including a chamber formed between two layers, for receiving fluid therein and for supporting users thereon, and including an inlet and an outlet, said mat device including a middle portion having a groove formed therein, and a seal formed around said groove, for allowing a user's head to engage through said groove of said mat device, and to engage said mat device onto the user, and means for pumping fluid into and out of said chamber of said mat device;

wherein said mat device includes at least one seal formed and provided therein for forming a fluid passage therein, said fluid passage of said mat device includes two ends communicating with said inlet and said outlet of said mat device;

wherein said groove of said mat device is U-shaped on a surface of the massage device and located close to said at least one seal of said mat device for forming a Y-shaped structure on a surface of the massage device;

said mat device includes a plurality of blocks disposed in said chamber thereof for narrowing said chamber of said mat device;

said blocks are secured between said layers of said mat device and having gaps formed between said blocks;

said pumping means includes a container for receiving the fluid and coupled to said inlet and said outlet of said mat device, and a pump for pumping the fluid into and out of said chamber of said mat device;

wherein the massage device further comprising a heat device disposed in said container for heating the fluid; a far infrared device disposed in said container for releasing far infrared material into the fluid and a processor device coupled to said pump for controlling said pump.

* * * * *